United States Patent [19]

Sistonen

[11] Patent Number: 4,955,933
[45] Date of Patent: Sep. 11, 1990

[54] DEVICE FOR MEASURING THE FRICTION ON A SURFACE

[76] Inventor: Matti Sistonen, Kalasääskentie 6 E 46, SF-02620 Espoo, Finland

[21] Appl. No.: 295,215
[22] PCT Filed: Jun. 25, 1987
[86] PCT No.: PCT/FI87/00087
§ 371 Date: Jan. 3, 1989
§ 102(e) Date: Jan. 3, 1989
[87] PCT Pub. No.: WO88/00337
PCT Pub. Date: Jan. 14, 1988

[30] Foreign Application Priority Data

Jul. 4, 1986 [FI] Finland .................................. 862834

[51] Int. Cl.$^5$ ............................................. G01N 19/02
[52] U.S. Cl. ........................................... 73/9; 73/146
[58] Field of Search ............................. 73/9, 146, 105

[56] References Cited

U.S. PATENT DOCUMENTS

| | | | |
|---|---|---|---|
| 2,821,081 | 1/1958 | Staples | 73/9 X |
| 2,946,644 | 7/1960 | Henry | 73/146 X |
| 3,367,170 | 2/1968 | Lynch et al. | 73/146 X |
| 4,594,878 | 6/1986 | Abe et al. | 73/146 X |

FOREIGN PATENT DOCUMENTS

| | | | |
|---|---|---|---|
| 852161 | 10/1952 | Fed. Rep. of Germany | 73/9 |
| 1059471 | 12/1983 | U.S.S.R. | 73/146 |
| 1095056 | 5/1984 | U.S.S.R. | 73/146 |

Primary Examiner—Hezron E. Williams
Assistant Examiner—Joseph W. Roskos
Attorney, Agent, or Firm—Andrus, Sceales, Starke & Sawall

[57] ABSTRACT

A device for measuring the friction on a surface, comprising a measuring wheel (1) and an arm (2) is attached to the wheel axle (3), and a spring (6) is attached between the measuring wheel (1) and its axle (3). The spring is arranged to resist the rotation of the measuring wheel (21), when the measuring wheel (1) is moved by the arm (2) on the surface (5) under measurement. The arm (2) is rigid and is provided with a straight part (8) which is permanently attached to the axle (3), and at the other end (2b) thereof there is provided a pull handle (4), the arm (2) is provided with an inclination indicator (9). In the measuring position, the straight part (8) of the arm (2) is kept parallel to the surface (5) under measurement. The pull handle (4) is then kept further than the radius (R) of the measuring wheel (1) with respect to the surface (5) and is rotatable about an axis parallel to the axle.

1 Claim, 2 Drawing Sheets

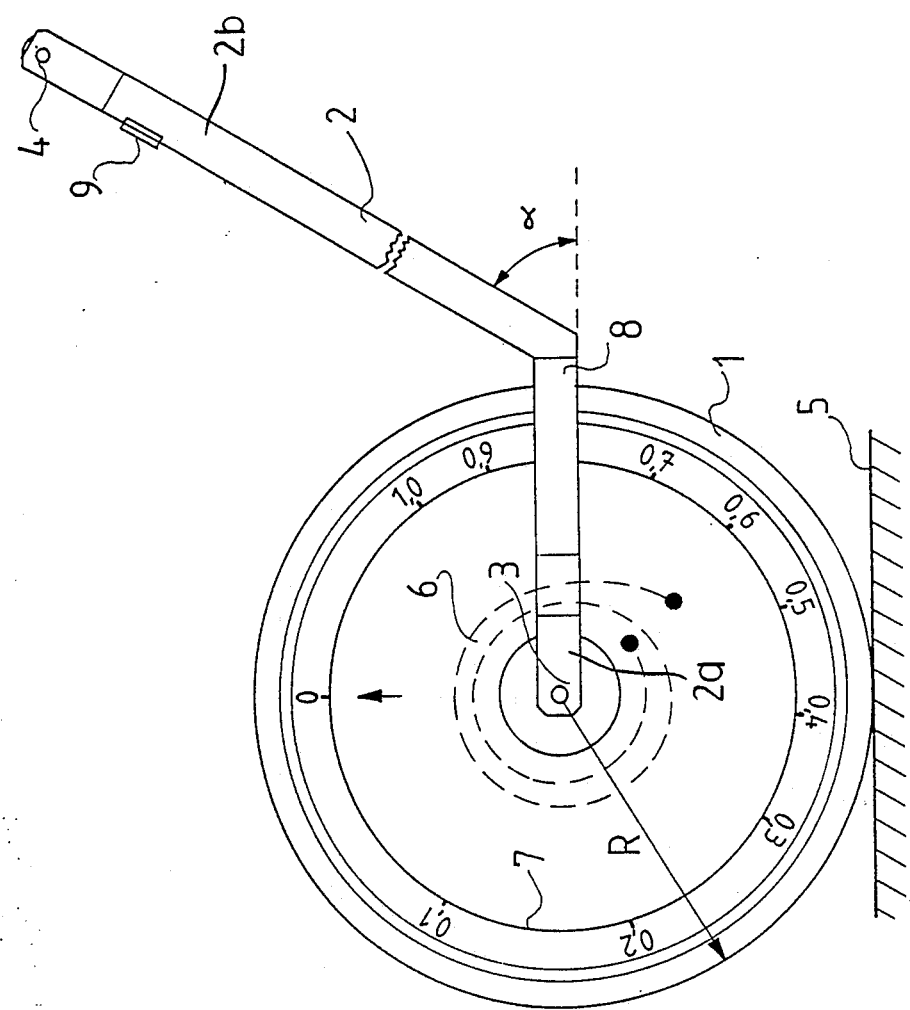

DEVICE FOR MEASURING THE FRICTION ON A SURFACE

BACKGROUND OF THE INVENTION

In the prior art there is known, from German published specification DE 852 161, a device for measuring the friction on a suface, wherein the first shaft moves a pair of wheels interconnected by means of an axis, which pair of wheels in turn move the measuring wheel by intermediation of another shaft. The second shaft, attached to the measuring wheel, is wound around the axis of the pair of wheels. In between the measuring wheel and the second shaft there is provided a spring, which retards the measuring wheel while the device is being moved. The degree of rotation of the measuring wheel at a point where the wheel starts to slide is comparable to the friction between the wheel and the base. The purpose of the pair of wheels is to make the attractive force directed to the measuring wheel parallel to the horizontal level, and it receives the vertical force component directed to the device due to the pulling.

The above described device is relatively large in size and is composed of several different components. Thus it is fairly sensitive to damage for instance during transport.

SUMMARY OF THE INVENTION

The object of the present invention is to simplify and to improve the device of the above described type in order to measure the friction on a surface. The device comprises a measuring wheel that is mounted for rotation about an axis and an arm is attached to the axis. A spring is connected between the measuring wheel and its axis and is arranged to resist rotation of the wheel when the wheel is moved on a surface to be measured by a handle attached to the arm.

Among the advantages of the measuring apparatus of the present invention, there is pointed out its simple structure, which means that the device is easy to carry along. Moreover, it is easily maintained, and the manufacturing costs are low.

DESCRIPTION OF THE DRAWINGS

In the following the invention is explained in detail with reference to the appended drawings, where FIG. 1 is a side-view illustration of the measuring device;

FIG. 2 is a front-view illustration of the measuring device; and

DESCRIPTION OF THE ILLUSTRATED EMBODIMENT

Figure 3:
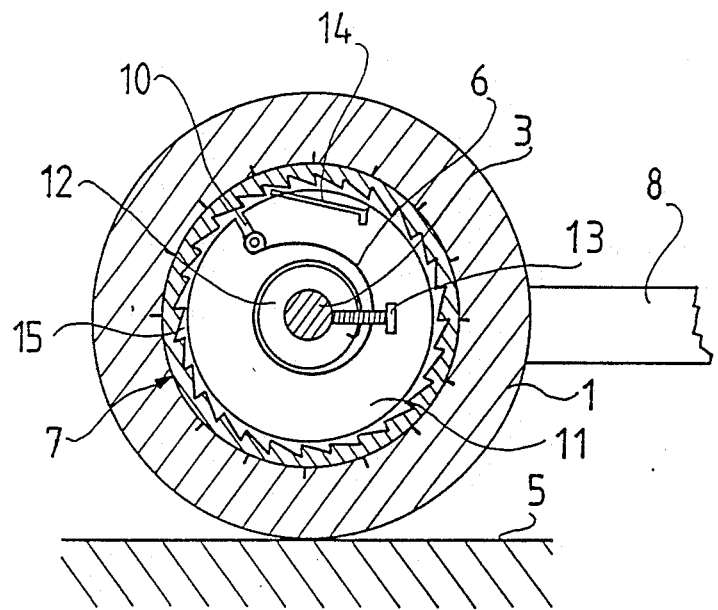
FIG. 3 illustrates the structure of the measuring wheel

In FIGS. 1 and 2, the device of the invention comprises the measuring wheel 1, the arm 2, the measuring wheel axis 3 and the spring 6. The measuring wheel 1 is free to rotate around its axis 3. The arm 2 is attached to the axis 3. The spring 6 is attached in between the measuring wheel 1 and its axis 3. The spring 6 is arranged to resist the rotation of the measuring wheel 1, when the measuring wheel 1 is moved by the arm 2 during the measuring operation on the surface 5 under measurement.

The arm 2 is stiff and uniform. At its first end 2a there is provided a straight part 8, which is permanently attached to the axis 2. At the second end 2b of the arm 1 there is provided the pull handle 4 or a corresponding member. The arm 2 is provided with an inclination indicator 9. In the measuring position, the angle of inclination $\alpha$ of the arm 2 is maintained, with respect to the surface 5 under operation, and the pull handle 4 is kept at a further distance than the radius R of the measuring wheel with respect to the surface 5. In order to help maintain the angle $\alpha$ of inclination constant, the arm is bent or folded, and its first part 8 starting from the axis 2 is in the correct position of the arm parallel to the surface 5.

The spring 6 resisting the rotation of the measuring wheel 1 can be attached to the measuring wheel for instance as is illustrated in FIG. 3. In this case the spring 6 is at one end fastened to the pin 10 provided in the measuring wheel, and at the other end to the protruding part 12 of the plate 11 wound around the axis 3. The rotation of the plate 11 can be prevented by means of the screw 13 which is attached to this protruding part 12.

While measuring friction, the measuring wheel 11 is pushed or pulled on the surface 5 under measurement. The rewinding of the measuring wheel is prevented by means of the spring bolt 14 and the indentation 15 provided on the inner circumference of the wheel 1. The tangential force caused by the tension of the spring 6 and resisting the rotation of the wheel is increased while the wheel is rotated. The tangential force caused by the spring 6 is compensated by the frictional force between the measuring wheel 1 and the surface 5. When there is achieved a situation where the frictional force cannot grow along with the tangential force caused by the tension of the spring 6, the wheel starts to slide. The journey of rotation of the wheel is comparable to the friction between the measuring wheel 1 and the surface 5. The rotation of the plate 11 around the axis 3 is prevented by means of the screw 13 while performing the measurement. The measuring wheel rotates freely when the screw 13 is screwed open. The spring bolt 14, which is at one end attached to the plate 11, prevents the rewinding or winding of the measuring wheel 1 after the wheel starts to slide in a measuring situation.

The measuring device is calibrated for example so that the friction coefficient of the surface 5 is directly readable on the scale 7. This may be arranged either on the inner circumference of the measuring wheel 1 or on the outer circumference of the plate 11. The tip of the spring bolt 14 indicates the reading in the preferred embodiment of FIG. 3. The display of the friction coefficient can naturally be arranged in some other fashion, too, for instance by means of an odometer. Then the friction coefficient is received, by intermediation of a wire cable, to a separate display unit in the vicinity of the pull handle 4.

The measuring device of the invention is operated as follows. The measuring wheel 1 is pulled, in this case by the handle 4, in a standing position, so that the handle is located above the axis 3 of the measuring wheel 1. Now a vertical force component is directed to the measuring wheel 1, which force component reduces the burden of the measuring wheel against the surface 5. When the angle of inclination of the arm 2 is maintained constant, which is carried out by observing the straight part 8 of the arm and/or by observing the inclination indicator 9, the reduction of the burden is always the same with a given tension of the spring 6. A change in the burden is taken into account on the reading scale 7 of the friction coefficient.

The arm 2 of the measuring wheel 1 forms a uniform, stiff shaft starting from the axis. At the end thereof there is provided the pull handle 4, which is advantageously wound in the longitudinal direction of the other end 1*b* of the arm. As a consequence of this arrangement, the measuring wheel 1 cannot be pressed by the arm 2 from the pull handle 4.

I claim:

1. A device for measuring the friction on a surface, comprising a measuring wheel to ride on said surface, an axle to rotatably support said measuring wheel, a rigid arm, said arm including a first section having a first end secured to said axle and having a second end, said first section of the arm being disposed substantially horizontal, said arm also including a second section connected to the second end of said first section and extending upwardly from said first section at an obtuse angle, spring means attached between the measuring wheel and the axle for resisting rotation of the measuring wheel when said measuring wheel is moved on said surface, inclination indicator means secured to said arm for indicating the inclination of said arm, a handle secured to the upper end of said second section of the arm, said handle being rotatable on the upper end of said arm about an axis parallel to said axle, said first and second sections of said arm being unsupported from said surface except for the connection to said measuring wheel.

* * * * *